United States Patent
Hu et al.

(10) Patent No.: US 11,096,789 B2
(45) Date of Patent: Aug. 24, 2021

(54) FEMORAL PROSTHESIS AND KNEE PROSTHESIS

(71) Applicants: BEIJING NATON MEDICAL TECHNOLOGY RESEARCH INSTITUTE CO. LTD., Beijing (CN); TIANJIN ZHENGTIAN MEDICAL INSTRUMENT CO., LTD., Tianjin (CN)

(72) Inventors: Senyuan Hu, Beijing (CN); Dayong Song, Beijing (CN); Xiang Dong, Beijing (CN); Shufu Xu, Beijing (CN); Zhihua Xu, Beijing (CN)

(73) Assignees: TIANJIN ZHENGTIAN MEDICAL INSTRUMENT CO., LTD., Tianjin (CN); BEIJING NATON MEDICAL TECHNOLOGY RESEARCH INSTITUTE CO. LTD., Beijing (CN)

( * ) Notice: Subject to any disclaimer, the term of this patent is extended or adjusted under 35 U.S.C. 154(b) by 0 days.

(21) Appl. No.: 15/929,280

(22) Filed: Apr. 22, 2020

(65) Prior Publication Data
US 2020/0330236 A1  Oct. 22, 2020

(30) Foreign Application Priority Data

Apr. 22, 2019 (CN) .......................... 201910325800.3
Sep. 26, 2019 (CN) .......................... 201910915324.0

(51) Int. Cl.
*A61F 2/38* (2006.01)

(52) U.S. Cl.
CPC ............ *A61F 2/3859* (2013.01); *A61F 2/389* (2013.01); *A61F 2002/3863* (2013.01)

(58) Field of Classification Search
CPC combination set(s) only.
See application file for complete search history.

(56) References Cited

U.S. PATENT DOCUMENTS

| 4,340,978 A | 7/1982 | Buechel et al. |
| 8,192,498 B2 | 6/2012 | Wagner et al. |

(Continued)

FOREIGN PATENT DOCUMENTS

EP         0993812       2/1999

OTHER PUBLICATIONS

Extended European Search Report dated Jun. 24, 2020 for Application No. 20170786.6, 7 pages.

*Primary Examiner* — Yashita Sharma
(74) *Attorney, Agent, or Firm* — Frost Brown Todd LLC

(57) ABSTRACT

A femoral prosthesis and a knee prosthesis are provided. The femoral prosthesis includes a condyle surface having a first surface section contacting a tibial joint surface over a first range of flexion angles and a second surface section contacting the tibial joint surface over a second range of flexion angles; the first range of flexion angles from a first to a second flexion angle; the second range of flexion angles from the second to a third flexion angle; the first flexion angle selected from −20° to 0°, the second flexion angle selected from 45° to 75°, the third flexion angle selected from 50° to 90° and the third flexion angle greater than the second flexion angle; the first surface section having a radius of curvature of a constant length, and the second surface section having a radius of curvature that decreases from a front end to the rear end.

14 Claims, 3 Drawing Sheets

(56) References Cited

U.S. PATENT DOCUMENTS

| | | | |
|---|---|---|---|
| 8,357,202 B2 | 1/2013 | Heggendorn et al. | |
| 2009/0326664 A1* | 12/2009 | Wagner | A61F 2/3836 623/20.21 |
| 2011/0153026 A1* | 6/2011 | Heggendorn | A61F 2/3859 623/20.35 |

* cited by examiner

FEMORAL PROSTHESIS AND KNEE PROSTHESIS

CROSS REFERENCE TO RELATED APPLICATIONS

This application claims priority to Chinese Patent Applications No. 201910915324.0, filed on Sep. 26, 2019, and No. 201910325800.3, filed on Apr. 22, 2019, the entire contents thereof are incorporated herein by reference.

TECHNICAL FIELD

The present disclosure relates to the technical field of medical devices, and in particular, to a femoral prosthesis and a knee prosthesis.

BACKGROUND

The knee is a joint with the most complex structure in the human body and more opportunities for injury. The aging of the human body and various joint diseases or traumas will cause partial or total damage to the knee motor function, resulting in joint pain and difficulty in movement. Knee prostheses are used to replace diseased or damaged knee joints of human, and use knee ligaments and soft tissues to enable patients to recover knee function and reduce pain. The knee prosthesis is usually designed into the approximate shape of a knee of human, and mimics the natural movement of the knee of human.

The above information disclosed in the background section is only used to enhance the understanding of the background of the present disclosure, so it may include information that does not constitute the prior art known to those of ordinary skill in the art.

SUMMARY

The femoral prosthesis includes a medial condyle portion and a lateral condyle portion, and the medial condyle portion and the lateral condyle portion each has a condyle surface for contacting a tibial joint surface. The tibial joint surface includes a joint surface of a natural meniscus, a tibial implant or a tibial bearing implant for contacting the femoral prosthesis.

According to an embodiment of the present disclosure, providing a femoral prosthesis which includes a medial condyle portion and a lateral condyle portion, and the medial condyle portion and the lateral condyle portion each having a condyle surface configured to contact the tibial joint surface, the tibial joint surface can comprise a joint surface of a natural meniscus, a tibial implant or a tibial bearing implant for abutting the femoral prosthesis.

The condyle surface of the medial condyle portion and the lateral condyle portion each having a first surface section for contacting the tibial joint surface over a first range of flexion angles, and a second surface section for contacting the tibial joint surface over a second range of flexion angles.

The first range of flexion angles is from a first flexion angle to a second flexion angle; the second range of flexion angles is from the second flexion angle to a third flexion angle; wherein the first flexion angle is in a range of –20 to 0°, the second flexion angle is in a range of 45 to 75°, the third flexion angle is in a range of 50 to 90° and the third flexion angle is greater than the second flexion angle.

The first surface section in the sagittal plane has a first radius of curvature of a constant length, and the second surface section in sagittal plane has a plurality of radii of curvature of decreasing length moving from a front end to a rear end of the second surface section.

In an exemplary embodiment of the present disclosure, the third flexion angle may exceed the second flexion angle by an amount in the range of 10° to 30°.

In an exemplary embodiment of the present disclosure, the second flexion angle may be in the range of 50° to 60°, and the third flexion angle may be in the range of 60° to 90°.

In an exemplary embodiment of the present disclosure, the first flexion angle is about 0°, the second flexion angle is about 60° and the third flexion angle is about 75°.

In an exemplary embodiment of the present disclosure, the second surface section includes a plurality of curved surfaces in which the radii of curvature in the sagittal plane decreasing sequentially from the front end to the rear end.

In an exemplary embodiment of the present disclosure, a difference between the radii of curvature of any two adjacent curved surfaces in the sagittal plane is not greater than 1 mm.

In an exemplary embodiment of the present disclosure, a radius of curvature of a curved surface at the rear end of the second surface section is a second radius of curvature, the second radius of curvature is the smallest radius of curvature of the second surface section, a ratio of the first radius of curvature of the first surface section to the second radius of curvature may be 1.3 to 2.1.

In an exemplary embodiment of the present disclosure, a ratio of the first radius of curvature to the second radius of curvature is 1.5-1.9.

In an exemplary embodiment of the present disclosure, a ratio of the first radius of curvature to the second radius of curvature is 1.5-1.7.

In an exemplary embodiment of the present disclosure, a plurality of curved surfaces of the second surface section on the sagittal plane ranges from 2 to 10 curved surfaces.

In an exemplary embodiment of the present disclosure, the number of the curved surfaces is 6.

In an exemplary embodiment of the present disclosure, each of the curved surfaces of the second surface section is configured to have the same central angle.

In an exemplary embodiment of the present disclosure, each of the curved surfaces of the second surface section is configured to have different central angle respectively.

According to the separate embodiment of the present disclosure, providing a knee prosthesis which includes the femoral prosthesis described above.

In an exemplary embodiment of the present disclosure, the knee prosthesis is an implant further comprising a tibial base and a tibial bearing. The tibial base is connected to a tibia; the tibial bearing is located between the femoral prosthesis and the tibial base, an upper surface of the tibial bearing is articulated with the femoral condyle surface of the femoral prosthesis, a lower surface of the tibial bearing is connected with the tibial base.

In the femoral prosthesis provided in the present disclosure, the first surface section of the condyle surface is a contact surface between the femoral prosthesis and the tibial joint surface during the gait movement of the human body, and has a radius of curvature of constant length in the sagittal plane to avoid abnormal relative movement of the joint surface caused by curved surface changes and to ensure the stability of joint motion. The second surface section is the part of the condyle surface that contacts with the tibial joint surface, when the knee is in high flexion, and the gradual decrease of the radius of curvature in the sagittal plane of the second surface section can maintain the stability of the movement of the knee under high flexion, and when the difference between the radius of curvature of the first surface section and the radius of curvature of the rear end of the second surface section can be larger, which can make the radius of curvature in the sagittal plane of the condyle surface (that is, the first surface section) that is in contact with the tibial joint surface during gait movement be larger, and maximize the contact area between the condyle surface and the tibial joint surface, reduce the contact stress between the condyle surface and the tibial joint surface, thereby effectively reducing joint wear. Walking is the most frequent movement of the knee joint (prosthesis), reducing the wear of the knee prosthesis during the walking can effectively increase the life of the prosthesis.

BRIEF DESCRIPTION OF THE DRAWINGS

The above described and other features and advantages of the present disclosure will become more apparent by describing the example embodiments in detail with reference to the accompanying drawings.

DETAILED DESCRIPTION

Figure 1:
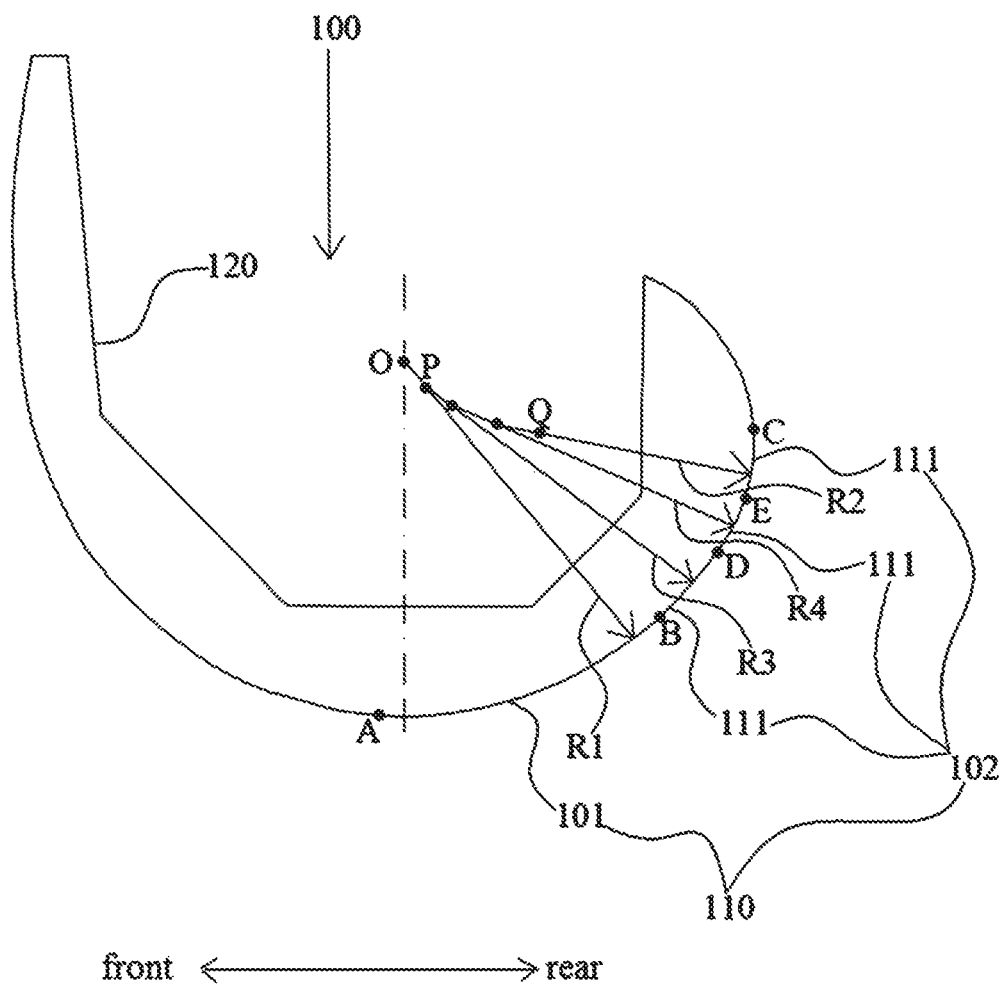
FIG. 1 is a cross-sectional view of a femoral prosthesis of the present disclosure in a sagittal plane.

Example embodiments will now be described more fully with reference to the accompanying drawings. However, the exemplary embodiments can be implemented in various forms and should not be construed as limited to the embodiments set forth herein; rather, these embodiments are provided so that this disclosure will be thorough and complete, and will fully convey the concept of example embodiments to those skilled in the art. The described features, structures, or characteristics may be combined in any suitable manner in one or more embodiments. In the following description, many specific details are provided to give a full understanding of the embodiments of the present disclosure.

The terms "first" and "second" are used only as markers, not as a limitation on the number of objects. The terms "radius of curvature" and "radii of curvature" in the present specification and claims refer to the radius of the circular arc which best approximates the curve at a given point of a curved surface, it is the reciprocal of the curvature as is known to those of skill in the art.

An embodiment of the present disclosure provides a femoral prosthesis, as shown in FIGS. 1 to 4, the femoral prosthesis 100 includes a condyle surface 110 for contacting a tibial joint surface, the condyle surface 110 has a first surface section 101 for contacting the tibial joint surface in the first range of flexion angles, and a second surface section 102 for contacting the tibial joint surface in the second range of flexion angles. The first range of flexion angles is from a first flexion angle to a second flexion angle; the second range of flexion angles is from the second flexion angle to a third flexion angle; In one embodiment, the first flexion angle is any flexion angle from −20 to 0°; the second flexion angle is any flexion angle from 45 to 75°; the third flexion angle is any flexion angle from 50 to 90°; and the third flexion angle is greater than the second flexion angle; the first surface section 101 on the sagittal plane has the first radius of curvature of a constant length, and the radii of curvature in the sagittal plane of the second surface section 102 decrease from the front end to the rear end of the second surface section. The front end of the second surface section 102 is adjacent to the first surface section 101.

Specifically, the femoral prosthesis includes a medial condyle portion and a lateral condyle portion, and the medial condyle portion and the lateral condyle portion each have a condyle surface 110 for contacting a tibial joint surface, the tibial joint surface includes the joint surface of the natural meniscus, the tibial implant or the tibial bearing implant for contacting the femoral prosthesis 100.

In the femoral prosthesis 100 provided in the present disclosure, the first surface section 101 is a contact surface between the femoral prosthesis 100 and the tibial joint surface during the gait movement of the human body, and has a single radius of curvature in the sagittal plane to avoid abnormal relative movement of the joint surface caused by curved surface changes and to ensure the stability of joint motion. The second surface section 102 is the part of the condyle surface 110 that contacts with the tibial joint surface in a high flexion state of the knee (for example, in a squatting state), and the gradual decrease of the radii of curvature of the second surface portion 102 in the sagittal plane can maintain the stability of the movement of the knee under high flexion, and when the difference between the radius of curvature of the first surface portion 101 and the radius of curvature of the rear end of the second surface section 102 can be larger, which can make the radius of curvature in the sagittal plane of the condyle surface 110 (that is, the first surface section 101) that is in contact with the tibial joint surface during gait movement be larger, and maximize the contact area between the condyle surface 110 and the tibial joint surface, reduce the contact stress between the condyle surface 110 and the tibial joint surface, thereby effectively reducing joint wear. Gait movement is the most frequent movement of the knee joint (prosthesis), thus, reducing the wear of the knee prosthesis during the walking can effectively increase the life of the prosthesis.

The following describes the components of the femoral prosthesis 100 provided in the embodiments of the present disclosure in detail with reference to the drawings.

In order to better explain and illustrated the technical solutions of the present disclosure, the directions, cut planes, etc. involved in the present disclosure are explained and illustrated in combination with the conventional description methods in the art.

In the field of anatomy and medical devices, the directions and planes such as inside, outside, front, rear, far, near, sagittal plane, coronal plane, and cross section have specific meanings, and are well known to those skilled in the art. Unless otherwise specified, these terms refer to the meanings recognized by those skilled in the art.

Generally, when describing the human body, joint or prosthesis, the following three sections are usually involved: sagittal plane, coronal plane z and cross section. Among them, the sagittal plane is a longitudinal section that divides the human body or joint into left and right parts along the front-rear direction, where the sagittal plane passing through the center of the human body is the median sagittal plane, which divides the human body into two equal parts. The coronal plane z refers to a longitudinal section that divides the human body or joint into front and rear parts along the left and right directions, the coronal plane z is perpendicular to the sagittal plane. The cross section is a plane that divides the human body or joint into upper and lower parts and parallels to the ground plane, and the cross section is perpendicular to the coronal plane z and the sagittal plane.

It can be understood that when describing a knee joint or a knee prosthesis, the sagittal plane, the coronal plane z, and the cross section all refer to the sections of an upright person, and the flexion angle is 0° at this time. When the knee joint or knee prosthesis is stretched or flexed, or when the posture of the human body is adjusted, the sagittal plane, the section may change accordingly.

Generally, when describing the human body, joint, or prosthesis, three different directions are involved: near and far, inside and outside, and front and rear. Among them, the far end refers to the end of the human body or joint that is relatively far away from the trunk. The near end refers to the end of the human body or joint that is relatively close to the trunk. The inside refers to the side that is relatively close to the median sagittal plane of the human body. The outside refers to the side that is relatively far from the median sagittal plane of the human body. The front side refers to the side that is relatively close to the abdomen on the sagittal plane. The rear side refers to the side relatively close to the back on the sagittal plane.

Figure 2:
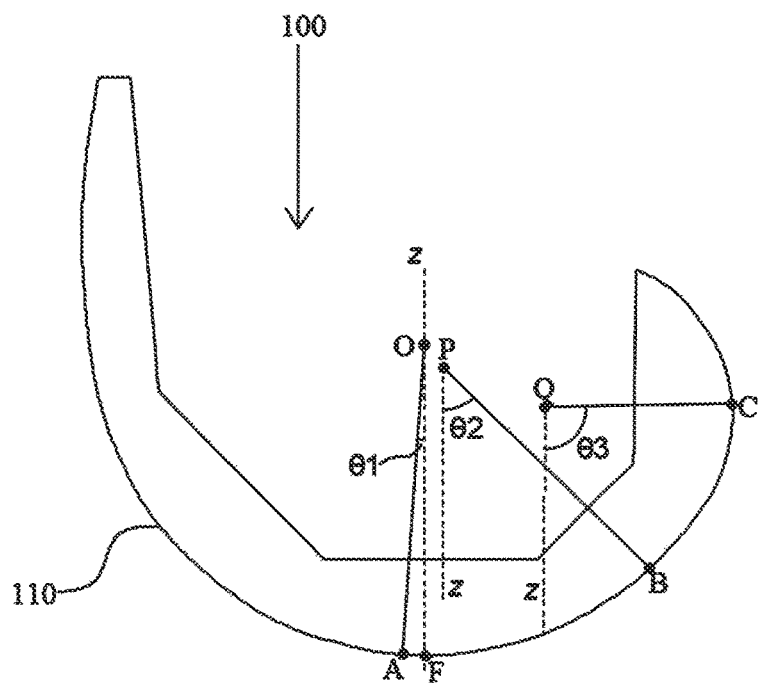
FIG. 2 is a cross-sectional view of a femoral prosthesis of one embodiment of the present disclosure in a sagittal plane showing the flexion angles.

As shown in FIG. 2, at a specific flexion angle, the condyle surface 110 contact the tibial joint surface, and the contact surface is a contact point or multiple consecutive contact points in the condyle surface 110 on the sagittal plane, referred to as "contact point". It can be understood that the contact points and the flexion angles correspond one-to-one, and those skilled in the art can determine the contact point or the circle center of each of the plurality of consecutive contact points of the condyle surface 110 on the sagittal plane at a specific knee flexion angle.

Where, the flexion angle at any contact point refers to the angle between the radius of curvature of the contact point on the sagittal plane and the coronal plane z. In other words, the condyle surface 110 appears as a curve on the sagittal plane, and the curve includes a contact point, and the curve has a tangent through the contact point, the angle between the perpendicular of the tangent on the sagittal plane and the coronal plane z is the flexion angle of the contact point. And when the flexion angle of the contact point is negative, it indicates that the contact point is located at the front end of the femoral prosthesis 100, and when the flexion angle at the contact point is positive, it indicates that the contact point is located at the rear end of the femoral prosthesis 100.

For example, as shown in FIG. 2, the first circle center O is the circle center of the radius of curvature of the first contact point A, the second circle center P is the circle center of the radius of curvature of the second contact point B, the third circle center Q is the circle center of the radius of curvature of the third contact point C. The line segment AO is the radius of curvature of the first contact point A, and the angle θ1 between the line segment AO on the sagittal plane and the coronal plane z is the flexion angle of the first contact point A. The line segment BP is the radius of curvature of the second contact point B, and the angle θ2 between the line segment BP on the sagittal plane and the coronal plane z is the flexion angle of the second contact point B. The line segment CQ is the radius of curvature of the third contact point C, and the angle θ3 between the line segment CQ on the sagittal plane and the coronal plane z is the knee flexion angle of the third contact point C. Thus, as shown the radius of curvature decreases as one moves from point B to point C in the second surface section 102.

Define the contact point F with flexion angle 0° as the reference contact point F, define the coronal plane z passing through the reference contact point F as the reference coronal plane z, the reference coronal plane z divides the femoral prosthesis 100 into two parts, a front part and a rear part. Where the front end of the femoral prosthesis 100 is located at the front side of the reference coronal plane z, and the rear end of the femoral prosthesis 100 is located at the rear side of the reference coronal plane z. When the contact point is located at the front end of the femoral prosthesis 100, the flexion angle of the contact point is negative; when the contact point is located at the rear end of the femoral prosthesis 100, the flexion angle of the contact point is positive.

It can be understood that any contact point refers to the point on the condyle surface 110 contacting with the tibial joint surface on the sagittal plane, and it does not mean that the condyle surface 110 and the tibial joint surface are necessarily already in contact at this contact point. In a single sagittal plane, the contact point may be point-shaped; and on the entire condyle surface 110, each of corresponding contact points may be connected into a line. In other words, the condyle surface 110 can be at least in line contact with the tibial joint surface, and the line becomes a contact point on the sagittal plane.

In the femoral prosthesis 100 provided in the present disclosure, as shown in FIG. 1, the condyle surface 110 is a smooth curve on the sagittal plane, and the smooth curve includes at least a first contact point A, a second contact point B and a third contact point C. The first surface section 101 is a curve between the first contact point A and the second contact point B on the sagittal plane; the second surface section 102 is a curve between the second contact point B and the third contact point C on the sagittal plane.

The first flexion angle is corresponded to the first contact point and in the range of −20° to 0°. The second flexion angle is corresponded to the second contact point and in the range of 45° to 75°. The third flexion angle is corresponded to the third contact point and in the range of 50° to 90°. The third contact point C is located on the rear side of the second contact point B, so that the third flexion angle is greater than the second flexion angle. The first radius of curvature of the first surface section 101 has the same length on the sagittal plane, and the radius of curvature on the sagittal plane of the second surface section 102 decreases from the front end to the rear end as one moves from contact point B to contact point C.

In one embodiment, the second flexion angle is in the range of 50° to 60°, and the third flexion angle is in the range of 60° to 90° to ensure the stability of the knee prosthesis under gait movement and increase radius of curvature of the contact surface on the sagittal plane during the walking to reduce the wear caused by frequent gait movement.

In one embodiment, the difference between the third flexion angle and the second flexion angle is 5° to 45°, so as to ensure that the curvature of condyle surface 110 between the second contact point B and the third contact point C is gentle and avoid abnormal movement of the joint surface caused by sudden curvature.

Further, the difference between the third flexion angle and the second flexion angle is 10° to 30°, so as to increase the change of curvature of the second surface section 102, and further ensure the stability of the knee joint in a high flexion state, so that the first surface section 101 can be set with a larger radius of curvature, thereby further reducing the contact stress between the condyle surface 110 and the tibial joint surface during the walking.

For example, in one embodiment of the present disclosure, the flexion angle corresponding to the first contact point A is 0°; the flexion angle corresponding to the second contact point B is 60°; and the flexion angle corresponding to the third contact point C is 75°. In the gait movement of the human body, the movement angle of the knee joint is generally in the range of 0° to 60°, and the knee joint is generally under the greatest pressure at this time. Therefore, walking is the most important and frequent movement of the knee joint, in this embodiment, the performance of the femoral prosthesis 100 is optimal in walking state.

Figure 3:
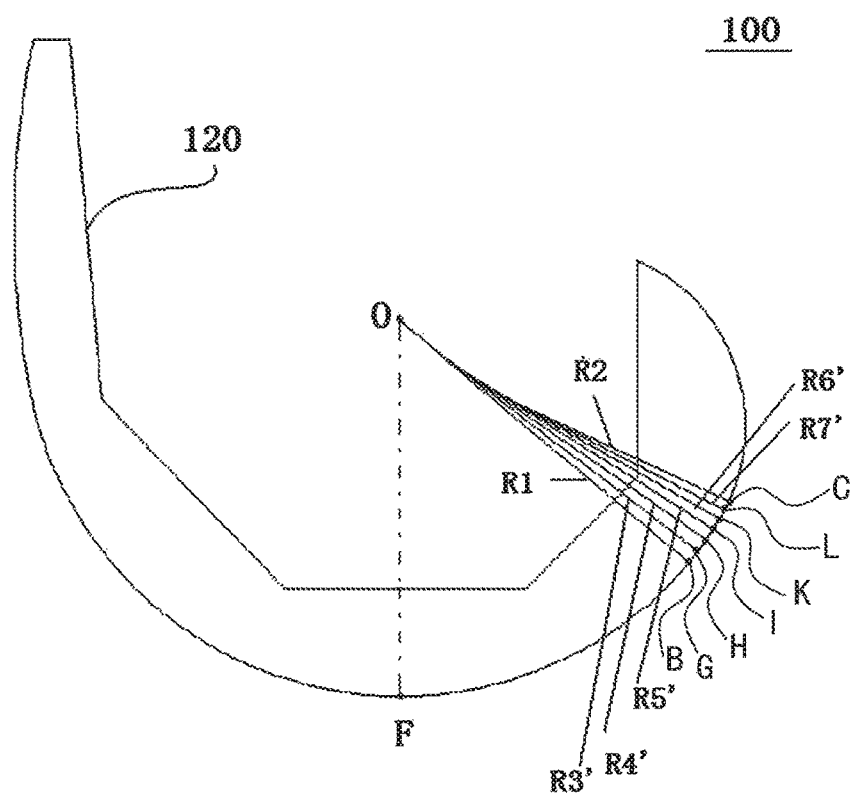
FIG. 3 is a cross-sectional view of a fermoral prosthesis of another embodiment of the present disclosure in the sagittal plane.

In one embodiment, the radius of curvature of the condyle surface is the same in the range of the flexion angle of 0° to 60°, the radius of curvature on the sagittal plane corresponds to the first radius of curvature R1 in the above embodiment. When the flexion angle is 75°, the radius of curvature of the condyle surface on the sagittal plane corresponds to the second radius of curvature R2 in the above described embodiment. In the embodiment, there are 5 different radii of curvature in the range of the flexion angle of 60° to 75°, as shown in FIG. 3, for example, the radii of curvature of R3', R4', R5', R6', R7' correspond to the contact points on the sagittal plane are G, H, I, K, L respectively, the five different radii of curvature and the second radius of curvature are gradually reduced, and the radius of curvature of the condyle surface on the sagittal plane is gradually changed from the first radius of curvature R1 to the second radius of curvature R2.

For another example, the flexion angle corresponding to the first contact point A is 0°, the flexion angle corresponding to the second contact point B is 60°, and the flexion angle corresponding to the third contact point C is 90°. In this way, the difference between the two ends of the second range of flexion angles is 30°, which is beneficial to set more curved surfaces with gradually curved in the condyle surface 110 between the second contact point B and the third contact point C, and further, it is more conducive to achieving a smoother curvature transition; it is also conducive to increasing the first radius of curvature R1, thereby increasing the contact area of the femoral prosthesis 100 with the tibial joint surface during the walking, reducing contact stress, and improving the life of the femoral prosthesis 100.

According to above design, a relatively large R1 can be used to ensure that the knee joint maintains the maximum contact area during the walking (within a flexion range of 0° to 60°), reduces contact stress, and effectively reduces the amount of wear during the walking. The multi-radius design of the second surface section at a flexion angle of 60° to 75° can avoid the abnormal forward movement of the femoral condyle caused by the mutation of the radius of curvature from R1 to R2. The design of multiple radii of curvature can achieve a gradual change from a large radius of curvature to a small radius of curvature to avoid abnormal forward movement.

In another embodiment of the present disclosure, the flexion angle θ1 of the first contact point A is 0°; the flexion angle θ2 of the second contact point B is 50°; and the flexion angle of the third contact point C θ3 is 60°.

The second surface section 102 includes a plurality of curved surfaces 111 in which the radius of curvature on the sagittal plane decreases sequentially from the front end to the rear end. Correspondingly, on the sagittal plane, the second surface section 102 may have a plurality of curves that are sequentially arranged from the front end to the rear end and the radius of curvature is sequentially reduced.

For example, as shown in FIG. 1, on the sagittal plane, the condyle surface 110 further has a fourth contact point D and a fifth contact point E between the second contact point B and the third contact point C, where the curved surface 111 between the second contact point B and the fourth contact point D has a third radius of curvature R3, and the curved surface 111 between the fourth contact point D and the fifth contact point E has a fourth radius of curvature R4. The curved surface 111 between the fifth contact point E and the third contact point C has a second radius of curvature R2. The first radius of curvature R1, the third radius of curvature R3, the fourth radius of curvature R4, and the second radius of curvature R2 decrease sequentially.

In one embodiment, the radius of curvature of the curved surface 111 at the rearmost end of the second surface section 102 is the second radius of curvature, which is also the shortest radius of curvature. The value of the difference between the radii of curvature of two adjacent curved surfaces 111 can be determined according to the difference between the first radius of curvature R1 and the second radius of curvature R2. The larger the difference between the first radius of curvature R1 and the second radius of curvature R2 is, the larger the difference between the radii of curvature of the two adjacent curved surfaces 111 may be; otherwise, the smaller the difference between the first radius of curvature R1 and the second radius of curvature R2 is, the smaller the difference between the radii of curvature of the two adjacent curved surfaces 111 may be. Of course, the difference between the radii of curvature of the two adjacent curved surfaces 111 can also be determined according to the number of curved surfaces 111 of the condyle surface 110 between the second contact point B and the third contact point C; the more curved surfaces 111 of the condyle surface 110 between the second contact point B and the third contact point C, the smaller the difference between the radii of curvature of two adjacent curved surfaces 111 may be; conversely, the fewer curved surfaces 111 of the condyle surface 110 between the second contact point B and the third contact point C, the larger the difference in radii of curvature between two adjacent curved surfaces 111 may be.

In an embodiment of the present disclosure, on the sagittal plane, the difference between the radii of curvature of the two adjacent curved surfaces 111 is not greater than 1 mm, so as to avoid abnormal movement of the joint surface caused by the large difference between the radii of curvature of two adjacent curved surfaces 111.

It can be understood that each curved surface 111 in the second surface section 102 on the sagittal plane may be a circular arc, and the central angle of each curved surface 111 is the same or different, as long as the difference between radii of curvature of the two adjacent curved surfaces 111 on the sagittal plane is reasonable to avoid joint movement instability.

In an embodiment of the present disclosure, a ratio of the first radius of curvature to the second radius of curvature may be 1.3 to 2.1. The smaller the ratio of the first radius of curvature to the second radius of curvature is, the smaller the change of the radius of curvature may be, which is beneficial to avoid abnormal movement of the joint surface caused by the large curvature of the second surface section 102; the larger the ratio of the first radius of curvature to the second radius of curvature is, the longer the first radius of curvature may be, which is conducive to increasing the contact surface area of the joint surface during the walking and reducing the wear of the joint prosthesis caused by frequent gait movement.

In one embodiment, the ratio of the first radius of curvature to the second radius of curvature is 1.5-1.9.

In one embodiment, the ratio of the first radius of curvature to the second radius of curvature is 1.5-1.7.

In one embodiment, the ratio of the first radius of curvature to the second radius of curvature is 1.55-1.65.

In one embodiment, on the sagittal plane, the number of the curved surfaces 111 of the condyle surface 110 between the second contact point B and the third contact point C is 2 to 10, that is, the number of the curved surfaces 111 of the second surface section is 2 to 10, in one embodiment, the number is 2 to 6. In this way, different curved surfaces 111 are provided with different radii of curvature, which can achieve a gentle transition from the first radius of curvature R1 to the second radius of curvature R2 of the condyle surface 110 and inhibit abnormal movement of the joint surface caused by a sudden change of curvature.

In another embodiment, the femoral prosthesis 100 of the present disclosure may further include an osteotomy surface 120 for connecting with the femur. The osteotomy surface 120 may be provided with one or more fixing column(s) 130 to achieve the tight connection and positioning of the femoral prosthesis 100 and the femur.

An embodiment of the present disclosure further provides a knee prosthesis, the knee prosthesis may include a femoral component for connecting with the femur, a tibial component for connecting with the tibia, and a tibial bearing positioned above the tibia component and articulated to the femoral component. The displacement of forward-backward and rotation of internal-external are generated between the support surface of the tibial bearing and condyle surface of the femoral component during the knee prosthesis is flexing and stretching. It is the main object in the design of knee prosthesis to ensure the stability of knee motion as much as possible and reduce the wear of knee prosthesis during the movement.

In one embodiment, the knee prosthesis includes any one of the femoral prosthesis 100 described in the above embodiment of the femoral prosthesis. The knee prosthesis may be a posterior cruciate ligament-retaining knee prosthesis, a posterior stability knee prosthesis, or another type of knee prosthesis. Since the knee prosthesis has any one of the femoral prosthesis 100 described in the above embodiment of the femoral prosthesis, it has the same beneficial effects, which will not be repeated here.

Figure 4:
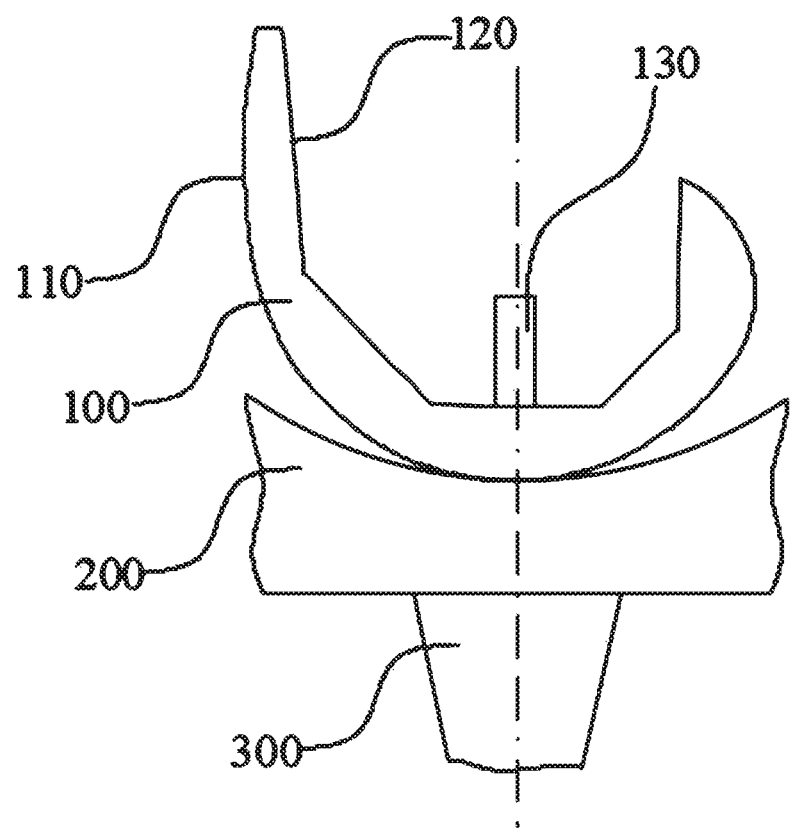
FIG. 4 is a cross-sectional view of a knee prosthesis and a femoral prosthesis of the present disclosure in the sagittal plane.

In one embodiment as shown in FIG. 4, the knee prosthesis of the present disclosure further includes a tibial base 300 connected to the tibia, and a tibial bearing 200 located between the femoral prosthesis 100 and the tibial base 300, the upper surface of the tibial bearing 200 is articulated with the condyle surface 110 of the femoral prosthesis 100, the lower surface of the tibial bearing 200 and the tibial base 300 may be connected in a rotating or fixed manner.

It should be understood that the scope of present disclosure does not limit with the detailed structure and arrangement of the components disclosed in embodiments. The present application also has other embodiments, and variations and modifications are within the scope of the present disclosure. It should be understood that the present also include all alternative combinations of two or more separate features mentioned or apparent in the text and/or drawings. All of these different combinations constitute various alternative embodiments of the present disclosure. The embodiments of this specification illustrate the best modes for implementing and will enable those skilled in the art to utilize the disclosure.

We claim:

1. A femoral prosthesis, comprising a condyle surface for contacting a tibial joint surface; the condyle surface having a first surface section for contacting the tibial joint surface over a first range of flexion angles, and a second surface section for contacting the tibial joint surface over a second range of flexion angles; the first range of flexion angles is from a first flexion angle to a second flexion angle; the second range of flexion angles is from the second flexion angle to a third flexion angle; wherein the first flexion angle is in a range of −20° to 0°, the second flexion angle is in a range of 45° to 75°, the third flexion angle is in a range of 50° to 90°, and the third flexion angle is greater than the second flexion angle; a first radius of curvature of the first surface section in a sagittal plane having a constant length, and a radius of curvature of the second surface section in sagittal plane decreasing length from a front end to a rear end of the second surface section; wherein the second surface section comprises a plurality of curved surfaces in which the radius of curvature in the sagittal plane decreases sequentially from the front end to the rear end; a radius of curvature of a curved surface at the rear end of the second surface section is a second radius of curvature, the second radius of curvature is the smallest radius of curvature of the second surface section, and characterized in that: a ratio of the first radius of curvature to the second radius of curvature is 1.5-1.9; wherein a difference between radii of curvature of any two adjacent curved surfaces of the second surface section in the sagittal plane is not greater than 1 mm.

2. The femoral prosthesis of the claim 1, wherein the third flexion angle exceeds the second flexion angle by an amount in the range of from 10° to 30°.

3. The femoral prosthesis of the claim 1, wherein the second flexion angle is in the range of from 50° to 60° and the third flexion angle is in the range of from 60° to 90°.

4. The femoral prosthesis of the claim 1, wherein the first flexion angle is 0°, the second flexion angle is 60° and the third flexion angle is 75°.

5. The femoral prosthesis of claim 1, wherein a ratio of the first radius of curvature to the second radius of curvature is 1.5-1.7.

6. The femoral prosthesis of claim 1, wherein the plurality of curved surfaces of the second surface section on the sagittal plane is from 2 to 10 curved surfaces.

7. The femoral prosthesis of claim 1, wherein the plurality of curved surfaces is 6.

8. The femoral prosthesis of claim 1, each of the plurality of curved surfaces of the second surface section is configured to have the same central angle.

9. The femoral prosthesis of claim 1, each of the plurality of curved surfaces of the second surface section is configured to have different central angle respectively.

10. A knee prosthesis, comprising a femoral prosthesis which comprises: a condyle surface for contacting a tibial joint surface; the condyle surface having a first surface section for contacting the tibial joint surface over a first range of flexion angles, and a second surface section for contacting the tibial joint surface over a second range of flexion angles; the first range of flexion angles is from a first flexion angle to a second flexion angle; the second range of flexion angles is from the second flexion angle to a third flexion angle; wherein the first flexion angle is in a range of −20° to 0°, the second flexion angle is in a range of 45° to 75°, the third flexion angle is in a range of 50° to 90° and the third flexion angle is greater than the second flexion angle; a first radius of curvature of the first surface section in the sagittal plane having a constant length, and a radius of curvature of the second surface section in sagittal plane having a decreasing length from a front end to a rear end of the second surface section wherein the second surface section comprises a plurality of curved surfaces in which the radius of curvature in the sagittal plane decreases sequentially from the front end to the rear end; a radius of curvature of a curved surface at the rear end of the second surface section is a second radius of curvature, the second radius of curvature is the smallest radius of curvature of the second surface section, and characterized in that: a ratio of the first radius of curvature to the second radius of curvature is 1.5-1.9; wherein a difference between radii of curvature of any two adjacent curved surfaces of the second surface section in the sagittal plane is not greater than 1 mm.

11. The knee prosthesis of claim 10, further comprising:
   a tibial base, connected to a tibia;
   a tibial bearing, located between the femoral prosthesis and the tibial base, an upper surface of the tibial bearing is articulated with the condyle surface of the femoral prosthesis, a lower surface of the tibial bearing connected with the tibial base.

12. The knee prosthesis of claim 10, wherein a difference between the third flexion angle and the second flexion angle is from 10° to 30°.

13. The knee prosthesis of claim 10, wherein the second flexion angle is in a range of from 50° to 60°, and the third flexion angle is in a range of from 60° to 90°.

14. The knee prosthesis of claim 10, wherein the first flexion angle is 0°, the second flexion angle is 60° and the third flexion angle is 75°.

\* \* \* \* \*